US008540716B2

(12) United States Patent
Sidebotham et al.

(10) Patent No.: US 8,540,716 B2
(45) Date of Patent: Sep. 24, 2013

(54) DISPOSABLE REAMER SHAFT OR MODULAR SPHERICAL OR TAPERED HOLLOW REAMER ASSEMBLY FOR MEDICAL APPLICATIONS

(76) Inventors: Christopher G. Sidebotham, Mendham, NJ (US); Randall J. Lewis, Bethesda, MD (US); Leon Roitburg, East Hanover, NJ (US)

( * ) Notice: Subject to any disclaimer, the term of this patent is extended or adjusted under 35 U.S.C. 154(b) by 560 days.

(21) Appl. No.: 12/583,873

(22) Filed: Aug. 27, 2009

(65) Prior Publication Data

US 2010/0168749 A1  Jul. 1, 2010

Related U.S. Application Data

(63) Continuation-in-part of application No. 12/072,671, filed on Feb. 27, 2008, which is a continuation-in-part of application No. 11/973,260, filed on Oct. 5, 2007, which is a continuation-in-part of application No. 11/704,754, filed on Feb. 9, 2007.

(51) Int. Cl.
*A61B 17/00* (2006.01)

(52) U.S. Cl.
USPC ............................................. 606/80

(58) Field of Classification Search
USPC ................................ 606/79–81, 84
See application file for complete search history.

(56) References Cited

U.S. PATENT DOCUMENTS

| 4,171,626 | A |   | 10/1979 | Yates | 464/181 |
|---|---|---|---|---|---|
| 4,248,062 | A |   | 2/1981 | McLain | 464/181 |
| 4,259,382 | A |   | 3/1981 | Schwan | 428/35.9 |
| 4,751,922 | A | * | 6/1988 | DiPietropolo | 606/80 |
| 4,793,363 | A | * | 12/1988 | Ausherman et al. | 600/567 |
| 4,811,632 | A |   | 3/1989 | Salyer | 76/115 |
| 5,100,267 | A |   | 3/1992 | Salyer | 407/54 |
| 5,116,165 | A |   | 5/1992 | Salyer | 407/54 |
| 5,171,312 | A |   | 12/1992 | Salyer | 606/81 |
| 5,171,313 | A |   | 12/1992 | Salyer | 606/86 |
| 5,236,433 | A |   | 8/1993 | Salyer | 606/91 |
| 5,282,804 | A |   | 2/1994 | Salyer | 606/86 |
| 5,299,893 | A |   | 4/1994 | Salyer | 407/54 |
| 5,501,686 | A |   | 3/1996 | Salyer | 696/79 |
| 5,527,159 | A | * | 6/1996 | Bozeman et al. | 417/45 |
| 5,658,290 | A |   | 8/1997 | Lechot | 606/80 |
| 5,709,688 | A |   | 1/1998 | Salyer | 606/81 |
| 5,720,749 | A | * | 2/1998 | Rupp | 606/79 |

(Continued)

FOREIGN PATENT DOCUMENTS

WO   WO/9007908   7/1990

*Primary Examiner* — Anu Ramana
(74) *Attorney, Agent, or Firm* — Ernest D. Buff; Ernest D Buff & Assoc. LLC; Dave Narasimhan

(57) ABSTRACT

A low cost disposable reamer shaft is made from a rod or tube stock of stainless steel, Nitinol or fiber reinforced polymer having a precise outer diameter in the range of 4 to 14 millimeter and is cut to a shaft length of 250 to 400 millimeters. An attachment piece with male or female thread matching a spherical hollow or tapered hollow reamer is machined and glued with epoxy on one end of the rod of tube stock using a precision centerline aligning jig. An attachment piece for connecting to a drive power unit is machined and glued with epoxy to the other end of the rod or tube stock thus forming a low cost disposable reamer shaft that aligns the centerline of the shaft with that of the reamer. The shaft contacts the reamer at two attachment locations that are displaced from each other, providing precise centerline alignment.

8 Claims, 4 Drawing Sheets

(56) References Cited

U.S. PATENT DOCUMENTS

| | | | |
|---|---|---|---|
| 5,755,719 A | 5/1998 | Frieze | 606/81 |
| 5,817,096 A | 10/1998 | Salyer | 606/81 |
| 5,976,144 A | 11/1999 | Fishbein et al. | 606/80 |
| 5,980,170 A | 11/1999 | Salyer | 408/239 R |
| 6,001,105 A | 12/1999 | Salyer | 606/81 |
| 6,015,411 A * | 1/2000 | Ohkoshi et al. | 606/80 |
| 6,168,600 B1 | 1/2001 | Grace et al. | 606/81 |
| 6,409,732 B1 | 6/2002 | Salyer | 606/91 |
| 6,428,543 B1 | 8/2002 | Salyer | 606/81 |
| 6,875,217 B2 | 4/2005 | Wolford | 606/81 |
| 2003/0181916 A1 | 9/2003 | Wolford | 606/81 |
| 2009/0088757 A1 | 4/2009 | Tulkis | 606/81 |

* cited by examiner

DISPOSABLE REAMER SHAFT OR MODULAR SPHERICAL OR TAPERED HOLLOW REAMER ASSEMBLY FOR MEDICAL APPLICATIONS

This is a Continuation-In-Part of application Ser. No. 12/072,671 filed on Feb. 27, 2008 for "Modular spherical hollow reamer assembly for medical applications" which is a Continuation-In-Part of application Ser. No. 11/973,260, filed Oct. 5, 2007 for "Modular Tapered Hollow Reamer For Medical Applications" which, in turn, is a Continuation-In-Part of application Ser. No. 11/704,754, filed Feb. 9, 2007, the disclosures of which are hereby incorporated in their entirety by reference thereto.

BACKGROUND OF THE INVENTION

1. Field of the Invention

The present invention relates to a disposable reamer shaft that may be attached to a modular disposable spherical or tapered hollow reamer, the disposable reamer shaft being concentrically attached to a modular hollow reamer to provide wobble free rotation of the reamer tool.

2. Description of the Prior Art

Reaming of the internal canal of bones is required in many surgical procedures of orthopedic surgery. These procedures include hip replacement and shoulder replacement, and the like. Reamers are used in procedures that involve creation of acetabular bone cavities that accept a properly sized acetabular cups. Prior art reamers typically fall into two major classes: rigid and flexible shaft. Typically, reaming of the internal bone cavity is achieved through utilization of a solid spherical reamer some having provisions for discharging and collecting reamed bone fragments. Solid spherical reamers currently utilized are required to cut both cancellous bone (spongy bone) and cortical bone (hard bone). Cortical bone is generally denser and stronger, requiring an efficient cutter to machine the acetabular cavity for a proper fit of the acetabular cup. Conventional spherical reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid spherical reamers are intended for multiple uses and therefore become less efficient after each surgery, resulting in poor cutting performance and bone necrosis. Dull blades also incorporate bone debris or bone cement debris into the living bone tissue, creating bone healing problems and fixation of an implanted acetabular cup.

U.S. Pat. Nos. 4,811,632, 5,100,267 and 5,299,893 to Salyer discloses a surgical reamer and a disposable acetabular reamer cup. The first patent does not disclose a disposable shaft while the second and third patents does not assure the concentricity of the cutting bowl with respect to that of the shaft.

U.S. Pat. No. 5,116,165 to Salyer discloses an acetabular reamer cup. This '165 patent does not have a disposable shaft and the arrangement used has no direct connection between the shaft and the cutting bowl other than through the base aperture. The concentricity of the cutting bowl with respect to that of the shaft is therefore not assured.

U.S. Pat. No. 5,658,290 to Lechot discloses an assembly comprising reamer spindle and reamer for surgery. The reamer comprises a cap and at least three radial rods which are arranged uniformly on the inside edge of the cap and join up integrally at the center of the cap. The reamer spindle comprises a shank on which there is fixed a reamer spindle head that is equipped with a bayonet with locking means for the securing of the reamer. The securing catches of the bayonet are intended to receive the radial rods of the reamer. The connection between the reamer rods and bayonet does not provide a precise centerline matching arrangement. The shaft is not indicated to be disposable U.S. Pat. No. 5,709,688, as well as U.S. Pat. Nos. 6,001,105, and 6,428,543 to Salyer disclose an acetabular reamer cup and method of producing the same. The bottom has a tool driver opening coaxial and is concentric with the cutting bowl. The driver opening engages with the shaft, which drives the acetabular reamer. This form of attachment of the shaft with the acetabular reamer does not ensure alignment of axis of the shaft with that of the acetabular reamer. The acetabular reamer or the shaft is not indicated to be disposable.

U.S. Pat. No. 5,755,719 to Frieze, et al. discloses an acetabular reamer. This acetabular reamer includes a base, a first set of semi-circular blades attached to the base, and a second set of semi-circular blades also contacting said base, and crossing and intersecting with said first set of blades at right angles thereto. The base preferably comprises a circular plate having a hexagonal drive hole in the center thereof and a plurality of slots in the periphery thereof for anchoring the blades. The drive shaft is coupled to a hexagonal aperture in the base plate. This method of attachment does not align the hemispherical cutter centerline with that of the drive shaft. As such, the arrangement causes wobbliness of the cutter in the bone cavity. The shaft of the acetabular reamer is not indicated to be disposable.

U.S. Pat. No. 5,976,144 to Fishbein et al. discloses a hollow dome reamer with removable teeth. A drive shaft is connected to the base plate through an aperture in the base plate and held in place by a spring. There is no direct attachment of the shaft to the dome and this multitude of connections to the shaft does not assure that the centerline of the shaft coincides with that of the hollow dome. The shaft is not indicated to be disposable.

U.S. Pat. No. 5,980,170 to Salyer as well as U.S. Pat. Nos. 5,817,096, 5,501,686, 5,282,804, 5,236,433, 5,171,313, 5,171,312 disclose a tool driver. This tool driver has a shaft with a longitudinal axis and opposite ends. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool, which is used with the driver has a bar which has the same dimensions as the groove in the boss of the tool driver of the invention. The bar thus fills the slot and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned. The tool driver has a shaft appointed to receive acetabular reamer cups and patella cutters. The cutters are appointed to be connected to the tip of the shaft by means of mounting bar in the cutter and a slot in the shaft secured by a complementary pin. This method of attachment—using a mounting bar that slides into a slot—does not align the centerline of the shaft with that of the reamer. Moreover, the shaft is not indicated to be disposable.

U.S. Pat. No. 6,168,600 to Grace, et al discloses an acetabular reamer backing plate and method of use. The backing plate for an acetabular reamer assembly that has a planar surface allows for the attachment of a reamer driver. This attachment feature only uses a single point attachment of the reamer to the shaft at the edge profile of the backing plate. It is therefore subject to displacement of the shaft laterally, causing the centerlines of the shaft and reamer to be not precisely aligned. The shaft is not indicated to be disposable.

U.S. Pat. No. 6,409,732 to Salyer discloses a tool driver. This tool driver has a shaft with a longitudinal axis and opposite ends. A boss is secured at one of the shaft ends by which the tool driver is connected to a rotary tool. A tool collate is secured to the other of the shaft ends by which the tool driver may be driven by a surgical hand piece having a chuck in which the collate may be positioned. The boss is equipped with a securing device of the bayonet type having a latch mechanism, which holds the rotary tool on the boss coaxially of the driver during use. The securing device has a tapered bore extending from the distal end of the boss axially of the shaft. The rotary tool has a diametrical bar extending across a bottom tool driver opening with a centrally located circular disk therein. The disk of the rotary tool fits within the bore of the tool shaft boss so as to concentrically locate the rotary tool and the tool shaft on the same axis. The latch mechanism holds the tool driver and the tool together in this position, whereby rotary tools of a multitude of sizes can be secured concentrically to the tool shaft without holding a plurality of critical tolerances when machining the bayonet type securing device or the rotary tool bottom bar. The tool driver is a shaft with a slot on the end that receives the acetabular reamer. It deals with the details of the device for attaching the acetabular reamer to the shaft. This type of slotted attachment does not result in coaxial mounting of the reamer that is coincident with the centerline of the shaft, even though the different components of the shaft are said to be coaxially aligned. The reamer or the shaft is not indicated to be disposable.

U.S. Pat. No. 6,875,217 to Wolford discloses an orthopedic reamer assembly. This orthopedic reamer assembly includes a reamer with a generally hemispherical shell having a concave side and at least one attachment feature associated with the concave side. A driver is attachable to the reamer and has a shaft with a reamer end. A releasable collar is disposed on the reamer end, which includes a boss having at least one retaining pin. A sleeve is fitted over the boss and includes a groove that is proximate to a corresponding retaining pin. The reamer has a cavity in the reamer end with a biasing element. The biasing element biases the sleeve in a closed position respective to the boss. A release pin, which press fits into the sleeve is provided in the reamer end, and is conveyed through the cavity, with the biasing element biasing against the release pin. The orthopedic reamer assembly is a complicated attachment of design of the drive shaft to an acetabular reamer with multiple sliding parts. Since each of the sliding parts requires a sliding fit, there are inherent displacement possibilities and therefore, the centerline of the shaft is not reliably aligned with the centerline of the acetabular reamer. Moreover, the acetabular reamer or the shaft is not indicated to be disposable and requires complicated machined elements to enable a sliding fit.

U.S. Patent Application Publication No. 2003/0181916 to Wolford discloses an orthopedic reamer with flat cutting teeth. This orthopedic reamer is for cutting bone and includes a shaft and a head coupled with the shaft. The head includes a distal face with a plurality of cutting teeth. Each cutting tooth includes a hole extending through the head. At least a portion of each hole has a substantially round perimeter. A raised lip is positioned adjacent to and extends around at least part of the substantially round portion. The '916 publication discloses an orthopedic reamer with flat cutting teeth having a shaft attached to acetabular reamer cups. The reamer cups or the shaft of the '916 publication are not disposable in nature. The attachment of the acetabular reamer to the drive shaft includes a complicated mechanism and does not reliably align the centerline of the drive shaft with that of the acetabular reamer. As such, wobble free rotation is not provided.

U.S. Patent Application Publication No. 2009/0088757 to Tulkis discloses an acetabular reamer. The reamer assembly includes a tool driver and a tool. Tool driver comprises a shaft. The tool receiving end of the shaft has a flange. Formed in the flange are four L-shaped bayonet catches, which receive the tool. The tool has a body having slots. A cutter can slidably fit into the slots. When installed in the slots, the cutters project slightly above the body. The projecting portions of the cutters form the cutting edges for shaving or cutting tissue. The reamer is formed by attaching a tool to the tool driver by lowering it in the L-shaped bayonet catches. The reamer can be coupled to a drive means such as a hand drill and inserted in a body cavity. Operating the reamer against body tissue shaves of body tissue. This type of four L-shaped bayonet catches attaching a shaft to a reamer does not provide precise alignment of the centerline of the reamer and the shaft since it is a single location attachment and is subject to rotational movement. The shaft is not indicated to be disposable.

Foreign Publication No. WO 9007908 to Schelhas discloses an acetabulum reamer. Acetabulum reamer for reaming the acetabulum of the human pelvic bone prior to insertion of an artificial hip joint cup comprises a reamer head on a shaft and a spiral reaming ridge arranged about the axis of the shaft and provided with reaming devices. The outer edge of the reaming ridge is delimited by a section of a spherical surface whose axis of rotation is flush with the axis of the shaft. The acetabulum reamer utilizes a spherical head for reaming a socket in an acetabulum. The spherical shape of the multiple use reamer provides the ability to hollow out the arcuate shape of the bone joints. Significantly, the acetabulum reamer publication does not teach a disposable spherical hollow surgical reamer tool that is attached to a drive shaft with coincident centerlines.

A number of prior art patents disclose use of polymeric shaft for delivering rotational torque. These polymeric shafts generally are tubular in construction with glass fibers or carbon fibers embedded in the polymer matrix. However, these polymeric shafts are rather large in diameter and short in overall length and generally unsuited for reamer shafts, which are required to be small in diameter and long in length.

U.S. Pat. No. 4,171,626 to Yates, et al. discloses a carbon fiber reinforced composite drive shaft. A carbon fiber reinforced composite tubular drive shaft has a plurality of bonded circumferentially disposed layers of fibrous reinforcement situated within an epoxy resinous matrix material. The innermost layer has glass fibers disposed at +30° to +50° to the longitudinal axis of the shaft. The outermost layer has glass fibers disposed at +60° to 90° to the longitudinal axis of said shaft. An intermediate layer has glass fibers disposed at 0° to +15° to the longitudinal axis of said shaft. An intermediate layer has carbon fibers disposed at 0° to +15° to the longitudinal axis of said shaft. The light weight composite drive shaft is resists torsion buckling to without deleteriously influencing the critical speed of the drive shaft. The drive shaft is not indicated to be for use in attaching hollow reamers.

U.S. Pat. No. 4,248,062 to McLain, et al. discloses a drive shaft assembly and method for making same. A composite drive shaft having a hollow tubular, multi-layered fiber reinforced plastic shaft portion with a metallic sleeve inserted in and bonded thereto at least at one end, said sleeve having a universal joint connector. The tubular, fiber-reinforced plastic shaft has layers of oppositely angled resin-impregnated helical fibers at 25° to 65° to the longitudinal shaft axis and at least one layer of longitudinal fibers forming a laminate and a metallic sleeve is received within at one end and longitudinal fibers provides flexural rigidity to the laminate and oppositely angled layers provide torsional strength and inner spiral layer provides additional hoop strength to the laminate. This drive shaft assembly has a universal joint and does not connect to a hollow reamer.

U.S. Pat. No. 4,259,382 to Schwan discloses fiber reinforced composite shaft with metal connector sleeves secured by adhesive. The tubular fiber reinforced composite shaft comprises a shaft body formed of a plurality of integrally bonded circumferential plies of solidified fiber reinforced resinous material. A metal sleeve is mounted in at least one end of the shaft body. A layer of adhesive material is disposed between an outer surface of the metal sleeve and an inner surface of the shaft body to bond the sleeve to the body. This composite shaft assembly with adhesively bonded is not indicated to connect to a hollow reamer.

There remains a need in the art for a modular easy-to-assemble spherical or tapered hollow reamer for medical applications having a disposable reamer shaft. Also needed in the art is a disposable spherical hollow or tapered cutter assembly, which can be attached concentric to a reusable shaft portion that provides means for reaming of a bone cavity without wobbly movement. Further needed in the art is a cutter assembly having means for collecting bone debris and keeping the collected debris displaced from the cutting portion, so that heat generated at the bone cutting surface is minimized. Still further needed in the art is a disposable shaft for a spherical hollow or tapered reamer assembly wherein, after one use of the spherical or tapered hollow reamer, a clean contamination-free replacement shaft is provided.

SUMMARY OF THE INVENTION

The present invention provides a disposable shaft for reamers. Reamer shafts are typically long with a shaft length in the range of 250 to 400 millimeters. These shafts have a small shaft diameter typically in the range of 4 to 14 millimeters, preferably 5 millimeters for hollow tattered reamers and 14 mm for spherical hollow reamers. The shaft must have certain features for the concentric attachment of the disposable shaft with a disposable modular hollow reamer. Moreover, the other side of the disposable shaft requires certain features for attachment to a drill or suitable drive drain. Machining such small-diameter long-length shafts with precision is generally difficult and time consuming; this results in reamer shaft cost that is well over thousand dollars. The shafts may be rigid or flexible depending on the type and orientation of the bone cavity being surgically reamed. The reamer shaft may be solid or cannulated, meaning that it has a central hole for inserting a guide pin.

Precisely dimensioned rods as well as tubes are readily available in the market place. Precision machining of small sized attachment pieces is readily carried out at a low manufacturing cost. The present invention contemplates attaching these small sized attachment pieces to a standard commercially available precision rods and tubes using gluing methods including use of epoxy glues in a fixture that creates precise alignment of the rod or tube shaft with the attachment pieces, one at each end. The attachment features may be affixed with an aperture drilled within the rod or affixed over the outside diameter of the rod or tube. Conveniently, the hole present within the tube may be used for affixing the attachment pieces. The attachment pieces are configured according to the attachment requirements of a specific modular reamer to which the disposable reamer shaft will be attached and may be a male threaded or female threaded screw attachment. The other side of the rod or tube is glued to an attachment piece that is a chuck drive, J&J drive or other driver that connects to other drive mechanisms.

Solid rigid shafts are made from precisely dimensioned rod stock of stainless steel or other suitable alloy or fiber reinforced plastic. Cannulated shafts are made from precisely dimensioned tubular stock. Flexible shafts solid or cannulated are made from Nitinol or fiber reinforced plastic. The fiber reinforced plastic may have fiber wraps surrounding a polymeric rod or tube that circumferentially reinforced for transmitting torque. The solid Nitinol shaft may be wire cut in a helical pattern to provide a spring like structure providing the desired flexibility. This wire cutting step may increase the reamer cost due to machining operation. However, when the shaft is required to be rigid additional fiber reinforcement is provided along the longitudinal length of the shaft to limit flexure. The reinforcing fibers may be selected from carbon filaments, boron filaments, glass fibers, polyaramid fibers (Kenval™), liquid crystal long chain polymer fibers (Spectra™) or combinations thereof.

Specifically, the attachment between the disposable spherical or tapered hollow reamer and the disposable shaft is accomplished by a precision threaded screw attachment at one end and a support feature at a distance away from the first threaded attachment location. This provides two attachment locations that are at a distance from each other providing precise rotational centerline alignment of the reamer shaft and the hollow reamer. The disposable reamer shaft has at one end a corresponding metallic fitting with precision threads adapted to connect to threads of the hollow reamer.

The process for manufacturing the low cost disposable reamer shaft for disposable spherical or tapered hollow reamer involves the following steps:
1. selecting a rod stock or tube stock with a precise outer diameter in the range of 4 to 14 millimeters;
2. cutting the rod or tube to required shaft length in the range of 250 to 400 millimeters for a disposable reamer shaft;
3. providing rod or tube end configuration for receiving attachment pieces;
4. machining attachment pieces with precise threads for attachment to a modular hollow reamer on one side and attachment pieces for attachment to drive power unit on one end, both types of pieces provided with an appropriate geometry for attachment for ends of a rod or tube; and
5. gluing with epoxy using a fixture that aligns centerlines a tube or rod with a modular hollow reamer attachment piece on one end and a drive connecting attachment piece of the other end;

wherein said low cost disposable reamer shaft is solid or flexible with or without cannulation is fabricated from stainless steel, reinforced plastic or Nitinol and is centerline matched to hollow reamer.

BRIEF DESCRIPTION OF DRAWINGS

The invention will be more fully understood and further advantages will become apparent when reference is had to the following detailed description of the preferred embodiments and the accompanying drawings, in which:

FIGS. 2A, 2B, 2C, 2B1, 2C1, and 2D illustrate cross sectional views depicting a first embodiment of a disposable reamer shaft attached to one design of disposable modular spherical hollow reamer;

FIGS. 3A, 3B, 3C, 3B1, 3C1, and 3D illustrate cross sectional views depicting a second embodiment of a disposable reamer shaft attached to another design of disposable modular spherical hollow reamer; and FIGS. 4A, 4B, 4C, 4D, 4E, 4C1, 4D1, 4E1 and 4F illustrate cross sectional views depicting a third embodiment of a disposable reamer shaft attached to a design of disposable modular tapered hollow reamer.

DESCRIPTION OF THE PREFERRED EMBODIMENTS

Figure 1:
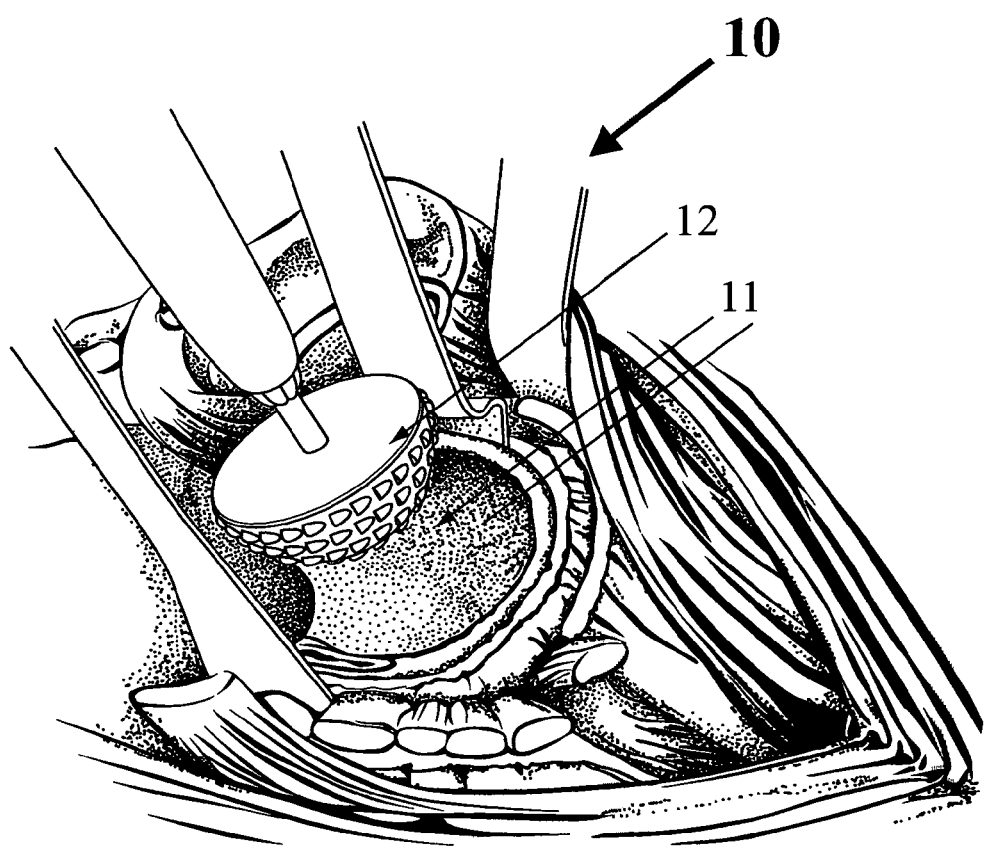
FIG. 1 Illustrates a cross sectional view depicting a first embodiment of a disposable reamer shaft attached to one design of disposable modular spherical hollow reamer.

In orthopedic surgery, total hip replacements require reaming the internal geometry of the acetabulum in order to establish a precise fit for the implant. This preparation can be intended for either cementing an acetabular cup (preparation would be oversized to the implant) or press fitting an acetabular cup (preparation undersized to the implant). In either case, a spherically shaped cutter is used to machine the internal geometry of the acetabulum. These spherical cutting tools are required to cut both cortical bone (hard bone) and cancellous bone (spongy bone) during normal surgery. The spherical cutter is generally assembled to a drive shaft which is coupled to a power drill and this assembly is used to machine the acetabulum for the implant. These cutters are intended for multiple surgeries and are used many times for many patients. The cutting action of these reamers is afforded by a plurality of cutting teeth. Because these teeth encounter hard bone and they are used multiple times, the cutters can become dull and inefficient in their cutting ability. Two primary problems exist with this type of instrument and surgical method:

1. Since these spherical cutters are reused, special attention is needed in properly cleaning them prior to use in preparing the next patient's acetabulum.

2. The cutting teeth can become dull even after one use and therefore do not cut bone efficiently. In addition, this cutting inefficiency generates friction/heat which can damage or kill the surrounding bone.

As these cutters become dull, they also do not cut an accurate preparation for the implant either in size or spherical geometry. Even initially, these cutters can be not accurately concentric which is further compounded by the wear and use of the cutter. Although these cutters are intended for multiple uses, there are really not quality control measures which monitor their function and eventual need to be replaced. There are not programs/qualified personnel in the hospitals that can inspect and evaluate the function and dimensional accuracy of the cutters after they have been used. It would be beneficial for the patient and the hospital to be assured that the surgeon could always be supplied with a clean/sterile spherical cutter with accurate and sharp cutting teeth for every clinical case.

Reaming of bone cavity is required during many orthopedic surgical procedures. These procedures include hip replacement and shoulder replacement and the like. Reaming of the bone cavities for the placement of an acetabular cup requires milling of precisely shaped bone cavity. When the acetabular cup is fixed by interference, this precision is more critical than when the acetabular cup is bonded to the bone cavity by a cement composition.

Generally stated, the disposable reamer shaft for disposable modular spherical or tapered hollow reamer for medical applications broadly comprises: (i) a disposable reamer shaft made from a rod or tube stock having precise outer diameter; (ii) one end of said rod or tube stock glued with epoxy or other suitable glue to a hollow reamer attachment piece that has appropriate affixing features portion at one end and threaded connection at its other end for attachment to said hollow reamer; (iii) other end of said rod or tube stock glued with epoxy or other suitable glue to power drive attachment piece that has appropriate affixing features portion at one end and chuck connection features on its other end.

The reamer shaft especially cannulated versions and flexible versions accumulate body fluids in the bent region as well as the cannulated central hole, which are impossible to clean contaminating the next patient when the reamer shaft is reused. The precision machining requirement of a long small diameter reamer shaft is very expensive resulting in reamer shaft cost in the range of several thousands of dollars. Therefore, it is desirable to provide a low cost disposable reamer shaft combating these contamination issues and reamer cost.

The disposable reamer shaft must be provided on one end with attachment features suited for attachment to disposable modular spherical or tapered hollow reamers with a precise centerline attachment. The other end of the disposable reamer shaft must have attachment features to connect the reamer shaft to a power drive unit. The disposable modular spherical hollow reamer disclosed in previously filed applications bearing Ser. Nos. 12/072,671 and 11/583,704 disclose two different geometries providing support of the modular spherical hollow reamer at two locations displaced at a distance from each other assuring concentric attachment of the reamer to the centerline of the shaft. The previously filed application bearing Ser. Nos. 11/973,260 and 11/583,691 discloses a geometry providing support of the modular tapered hollow reamer at two locations displaced at a distance from each other assuring concentric attachment of the reamer to the centerline of the shaft. These arrangements of the disposable reamer shaft are disclosed in FIGS. 2 through 4 below.

Figure 2:
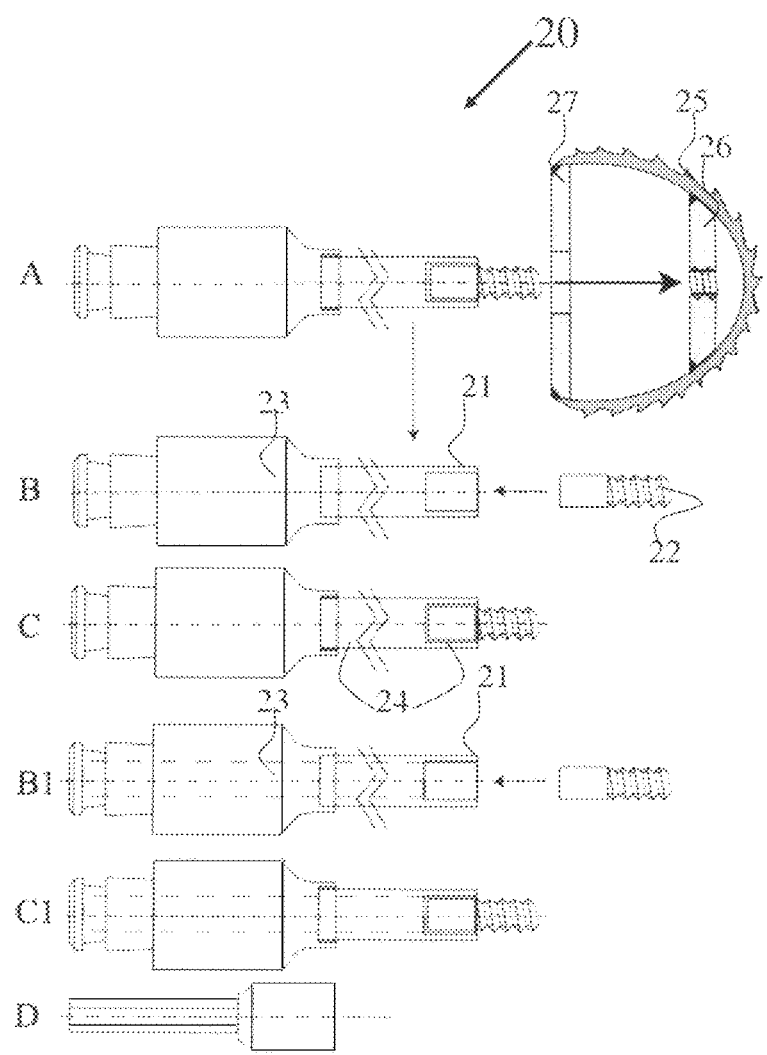

FIG. 2 Illustrates at 20 a cross sectional view depicting a first embodiment of a disposable reamer shaft attached to one design of disposable modular spherical hollow reamer. The right side of the sub figure of FIG. 2 marked A depicts the manufactured disposable spherical hollow reamer. It has a cutting spherical shell 25 with a welded first plate at 26 having a threaded aperture and a second welded plate 27 with a central aperture. The drive shaft 21 for this disposable modular spherical hollow reamer is shown to be a solid rod in the sub figure of FIG. 2, marked B and as a tube in the sub figure of FIG. 2, marked B1 representing a cannulated disposable reamer shaft. In both cases, the right side of the rod or tube has a milled aperture to receive the modular hollow reamer attachment piece 22, which is glued by epoxy at 24. The other end of the rod or tube 21 is glued to a J&J drive chuck 23 also using epoxy glue at 24. Note that the J&J drive chuck 23 slides over the rod or tube 21 creating the disposable reamer shaft. The finished disposable reamer shaft is shown at sub-figure of FIG. 2, marked at C for a solid shaft and at C1 for a cannulated shaft. A chuck drive is shown at subfigure of FIG. 2, marked D. The attachment piece 22 screws into the aperture of the first welded plate 26, a first attachment point for the disposable reamer shaft. The sliding of the outer surface inside the aperture of second welded plate 27 provides a second attachment point. These two displaced attachment locations provide precise alignment of the centerline disposable reamer shaft with that of the modular spherical hollow reamer.

Figure 3:
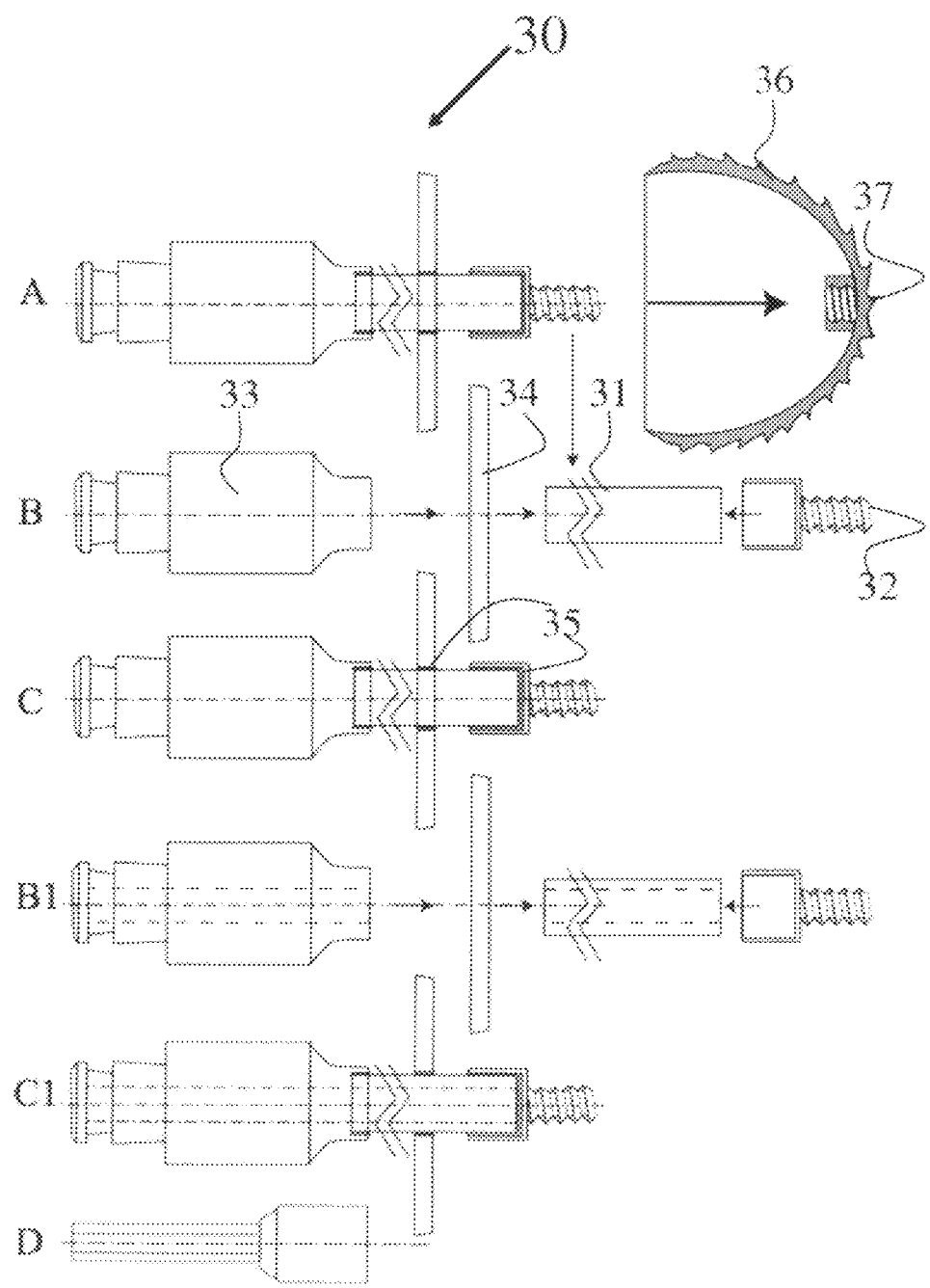

FIG. 3 Illustrates at 30 a cross sectional view depicting a second embodiment of a disposable reamer shaft attached to one design of disposable modular spherical hollow reamer. The right side of the sub figure of FIG. 3, marked A depicts the manufactured disposable spherical hollow reamer. It has a cutting spherical shell 36 has a welded female screw thread at 37. The drive shaft 31 for this disposable modular spherical hollow reamer is shown to be a solid rod in the sub figure of FIG. 3, marked B and as a tube in the sub figure of FIG. 3, marked B1 representing a cannulated disposable reamer shaft. In both cases, the left side of the modular reamer attachment piece 32 has a milled aperture to receive right side of the rod or tube 31, which is glued by epoxy at 35. A tapered conical element 34 is also glued by epoxy to the shaft as shown at 35 and slides over the interior of the spherical dome of the reamer 36. The other end of the rod or tube 31 is glued to a J&J drive chuck 23 also using epoxy glue at 24. The finished disposable reamer shaft is shown at subfigure of FIG. 3, marked at C for a solid shaft and at C1 for a cannulated shaft. The attachment piece 32 screws into the threaded aperture 37, a first attachment point for the disposable reamer shaft. The sliding of the outer surface of glued plate 34 inside the spherical dome of spherical reamer 36 provides a second attachment point. These two displaced attachment locations provide precise alignment of the centerline disposable reamer shaft with that of the modular spherical hollow reamer. A chuck drive is shown at subfigure of FIG. 3, marked D.

Figure 4:
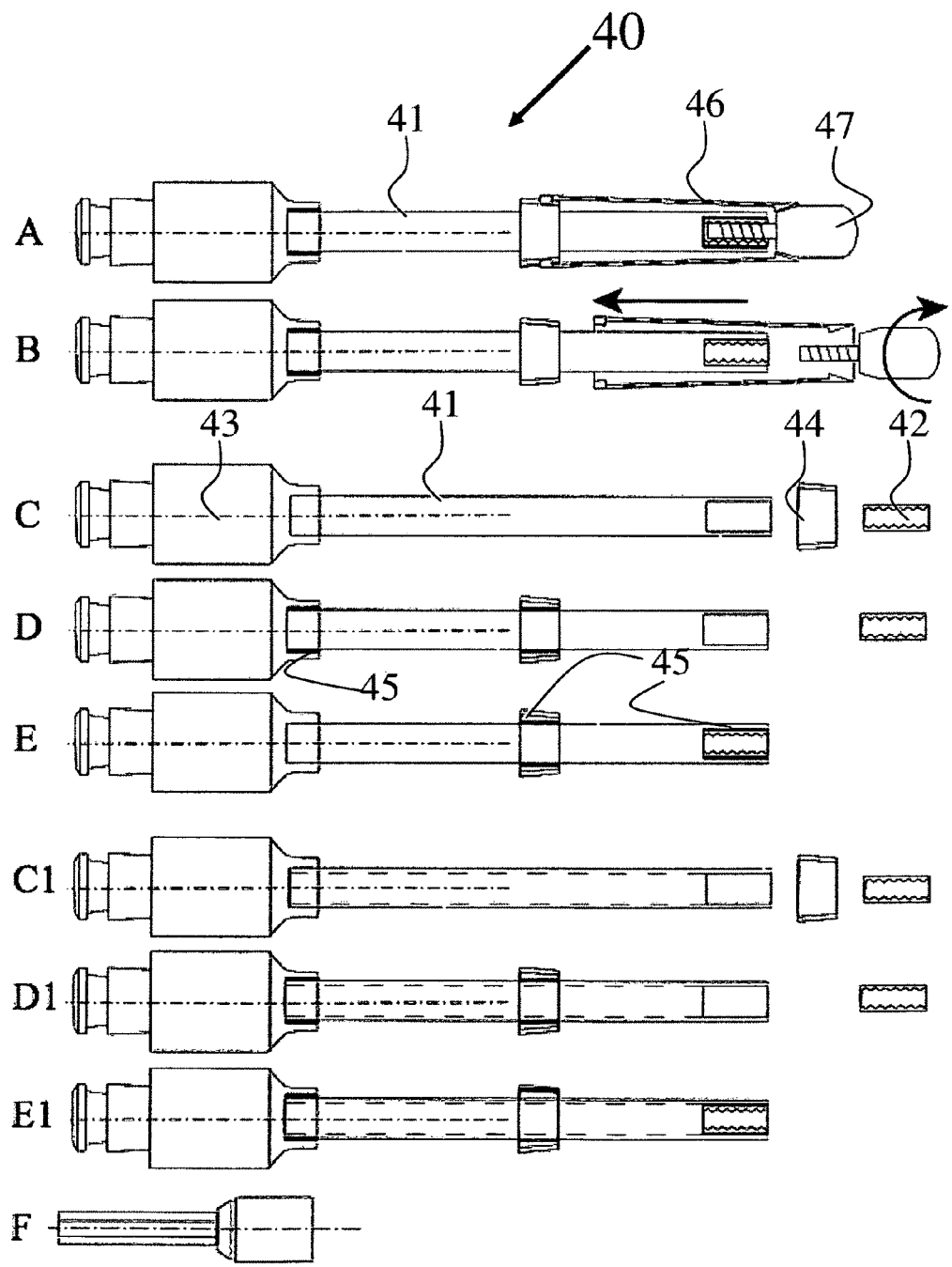

FIG. 4 Illustrates at 40 a cross sectional view depicting a third embodiment of a disposable reamer shaft attached to a disposable modular tapered hollow reamer. The right side of the sub figure of FIG. 4, marked A depicts the assembled modular tapered hollow reamer with a finished shaft. The sub figure of FIG. 4, marked B depicts how the tapered hollow reamer is disassembled. The drive shaft 41 for this disposable modular tapered hollow reamer is shown to be a solid rod in the sub figure of FIG. 4, marked C and as a tube in the sub figure of FIG. 4, marked C1 representing a cannulated disposable reamer shaft. In both cases, the right side of rode or tube 41 has a milled aperture to receive the left side of the attachment piece 42, which is glued by epoxy at 45. A tapered conical element 44 is also glued by epoxy to the shaft as shown at 45 and contacts the interior of the tapered hollow reamer 46. The other end of the rod or tube 41 is glued to a J&J drive chuck 43 also using epoxy glue at 45. The sub figure of FIG. 4, marked D, depicts a solid shaft with said tapered conical element being glued thereon. Likewise, the sub figure of FIG. 4, marked D1, depicts a cannulated shaft with said tapered conical element being glued thereon. The finished disposable reamer shaft is shown at subfigure of FIG. 4, marked at E for a solid shaft and at E1 for a cannulated shaft. The attachment piece 42 screws into the threaded male screw of the pilot 47, a first attachment point for the disposable reamer shaft. The attachment of the conical outer surface of glued element 44 inside the tapered hollow reamer 46 provides a second attachment point. These two displaced attachment locations provide precise alignment of the centerline disposable reamer shaft with that of the modular tapered hollow reamer. A chuck drive is shown at sub figure of FIG. 4, marked F.

The key features of the low cost disposable reamer shaft for spherical or tapered hollow reamer for medical applications include, in combination, the components set forth below:
a) the disposable reamer shaft made from precision sized rod or tube with glued precisely machined attachment pieces on either end using a fixture that aligns centerlines during gluing;
b) each rod or tube receiving one attachment piece at each end one made to fit a modular spherical or tapered reamer and other providing an attachment to chuck of power drive;
c) said rod is solid and or a tube that is flexible;
d) said rod or tube is cannulated and rigid or flexible;
e) said solid rod or tube is made from stainless steel or fiber reinforced polymer with fiber extending along longitudinal and circumferential directions;
f) said flexible rod or tube is made from Nitenol or fiber reinforced polymer with fiber extending along circumferential direction;
g) said reinforcing fiber selected from carbon fibers, boron fibers, steel fibers, polyaramid (Kevlar), liquid crystal polymer fibers (Spectra™) or combinations thereof;
whereby the reamer shaft provides precise alignment of the centerline of the reamer shaft with that of the modular spherical or tapered hollow reamer.

The manufacturing process for the low cost disposable reamer shaft comprises the following manufacturing steps;
1. selecting a rod stock or tube stock with a precise outer diameter in the range of 4 to 14 millimeters;
2. cutting the rod or tube to required shaft length in the range of 250 to 400 millimeters for a disposable reamer shaft;
3. providing a rod or tube end configuration for receiving attachment pieces;
4. machining attachment pieces with precise threads for attachment to a modular hollow reamer on one side and attachment pieces for attachment to drive power unit on one end, both types of pieces provided with an appropriate geometry for attachment for ends of a rod or tube; and
5. gluing with epoxy using a fixture that aligns centerlines a tube or rod with a modular hollow reamer attachment piece on one end and a drive connecting attachment piece of the other end;
wherein said low cost disposable reamer shaft is solid or flexible with or without cannulation is fabricated from stainless steel, Nitinol or reinforced polymer and is centerline matched to hollow reamer.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A disposable low cost reamer shaft for a spherical or tapered hollow reamer assembly for medical applications, comprising:
a. the disposable reamer shaft made from a precision sized rod or tube;
b. said rod being glued with precisely machined attachment pieces, one on each end, using a fixture that aligns centerlines during gluing;
c. one end of said rod or tube receiving a first attachment piece made to fit a modular spherical or tapered hollow reamer;
d. a second end of said rod or tube receiving a second attachment piece made to fit to a chuck of a power drive;
e. a support located on said reamer shaft proximate to said first attachment piece, said support and said first attachment piece being appointed to engage with said modular spherical or tapered hollow reamer, thereby providing two displaced attachment locations in order to align and attach said reamer shaft to said modular spherical or tapered hollow reamer; and f. said first attachment piece having male or female threads that are adapted to connect to threads located on said modular spherical or tapered hollow reamer; whereby the reamer shaft provides precise alignment of the centerline of the reamer shaft with that of the modular spherical or tapered hollow reamer.

2. A disposable low cost reamer shaft for medical applications as recited by claim 1, wherein said rod or tube has an outer surface diameter in the range of 4 mm to 14 mm.

3. A disposable low cost reamer shaft for medical applications as recited by claim 1, wherein said rod or tube has a length in the range of 250 mm to 400 mm.

4. A disposable low cost reamer shaft for medical applications as recited by claim 1, wherein said rod is solid and is made from stainless steel or a fiber reinforced polymer.

5. A disposable low cost reamer shaft for medical applications as recited by claim 1, wherein said rod is flexible and is made from Nitenol or a fiber reinforced polymer.

6. A disposable low cost reamer shaft for medical applications as recited by claim 1, wherein said glue is an epoxy resin.

7. A disposable low cost reamer shaft for medical applications as recited by claim 1, wherein said support comprises a plate.

8. A disposable low cost reamer shaft for medical applications as recited by claim 1, wherein said support comprises a tapered conical element.

* * * * *